(12) United States Patent
Mohl

(10) Patent No.: US 11,241,238 B2
(45) Date of Patent: *Feb. 8, 2022

(54) TREATING HEART TISSUE

(71) Applicant: Miracor Medical SA, Awans (BE)

(72) Inventor: Werner Mohl, Altenmarkt-Thennenberg (AT)

(73) Assignee: Miracor Medical SA, Vienna (AT)

( * ) Notice: Subject to any disclaimer, the term of this patent is extended or adjusted under 35 U.S.C. 154(b) by 1565 days.

This patent is subject to a terminal disclaimer.

(21) Appl. No.: 13/925,107

(22) Filed: Jun. 24, 2013

(65) Prior Publication Data

US 2013/0282042 A1    Oct. 24, 2013

Related U.S. Application Data

(60) Continuation of application No. 13/549,585, filed on Jul. 16, 2012, which is a division of application No. 12/786,785, filed on May 25, 2010.

(51) Int. Cl.
*A61B 17/12* (2006.01)
*A61M 25/10* (2013.01)
(Continued)

(52) U.S. Cl.
CPC .... *A61B 17/12136* (2013.01); *A61B 17/1204* (2013.01); *A61B 17/12109* (2013.01); *A61M 25/10184* (2013.11); *A61M 25/10188* (2013.11); *A61B 5/0215* (2013.01); *A61B 2017/00199* (2013.01); *A61B 2017/00243* (2013.01);
(Continued)

(58) Field of Classification Search
CPC .... A61B 17/12109; A61B 2017/22001; A61B 17/12022; A61B 17/1204; A61B 17/12122; A61B 17/12136; A61B 2017/00172; A61B 2017/00199; A61M 25/10; A61M 25/10184; A61M 25/10188; A61M 2210/125; A61M 1/10; A61M 1/1005; A61M 1/122; A61M 1/1072;
(Continued)

(56) References Cited

U.S. PATENT DOCUMENTS 4,016,871 A    4/1977   Schiff
4,459,977 A *  7/1984   Pizon .................... A61M 1/106
                                                              600/16

(Continued)

FOREIGN PATENT DOCUMENTS

UA          14911 U     6/2006
WO      WO 8910155     11/1989

OTHER PUBLICATIONS

Glogar, D. H., W. Mohl, and H. Mayr. "Pressure Controlled Intermittent Coronary Sinus Occlusion Effects the Myocardium at Risk and Reduces Infarct Size." The Coronary Sinus (1984): 445-53. Web.*

(Continued)

*Primary Examiner* — Tuan V Nguyen
(74) *Attorney, Agent, or Firm* — Fish & Richardson P.C.

(57) ABSTRACT

Some systems and methods for treating heart tissue may include instruments for intermittently occluding the coronary sinus using a coronary sinus occlusion catheter device. In some embodiments, the coronary sinus occlusion catheter can be used before or during a coronary intervention procedure in which a blockage in a heart is repaired or removed.

17 Claims, 9 Drawing Sheets

(51) Int. Cl.
  *A61F 2/958* (2013.01)
  *A61B 17/00* (2006.01)
  *A61M 25/00* (2006.01)
  *A61B 5/0215* (2006.01)
  *A61F 2/95* (2013.01)

(52) U.S. Cl.
  CPC ......... *A61F 2/95* (2013.01); *A61F 2002/9583* (2013.01); *A61M 25/007* (2013.01); *A61M 25/1002* (2013.01); *A61M 2025/0003* (2013.01); *A61M 2025/1052* (2013.01)

(58) Field of Classification Search
  CPC .............. A61M 1/3613; A61M 1/3604; A61M 25/1018; A61M 1/107
  See application file for complete search history.

(56) References Cited

U.S. PATENT DOCUMENTS

| | | | | |
|---|---|---|---|---|
| 4,493,697 A * | 1/1985 | Krause | ................ | A61B 5/0456 600/18 |
| 4,589,869 A | 5/1986 | Wernborg | | |
| 4,657,536 A | 4/1987 | Dorman | | |
| 4,671,796 A | 6/1987 | Groshong et al. | | |
| 4,697,574 A | 10/1987 | Karcher | | |
| 4,701,166 A | 10/1987 | Groshong et al. | | |
| 4,705,501 A | 11/1987 | Wigness et al. | | |
| 4,887,608 A * | 12/1989 | Mohl | ................ | A61M 1/1072 600/486 |
| 4,934,996 A | 6/1990 | Mohl et al. | | |
| 4,943,277 A | 7/1990 | Bolling | | |
| 4,969,470 A * | 11/1990 | Mohl | ................ | A61M 1/1072 600/486 |
| 5,011,468 A * | 4/1991 | Lundquist | ........... | A61M 1/3613 600/16 |
| 5,024,668 A * | 6/1991 | Peters | ................ | A61M 1/3621 600/18 |
| 5,033,998 A * | 7/1991 | Corday | ............. | A61M 25/1002 600/18 |
| 5,156,600 A | 10/1992 | Young | | |
| 5,224,938 A | 7/1993 | Fenton, Jr. | | |
| 5,226,427 A | 7/1993 | Buckberg et al. | | |
| 5,324,260 A * | 6/1994 | O'Neill | ............. | A61M 25/0068 604/103.08 |
| 5,458,574 A | 10/1995 | Machold et al. | | |
| 5,466,216 A | 11/1995 | Brown et al. | | |
| 5,533,957 A | 7/1996 | Aldea | | |
| 5,707,358 A * | 1/1998 | Wright | ............... | A61M 25/1011 604/103.07 |
| 5,755,686 A | 5/1998 | O'Neill et al. | | |
| 5,779,685 A * | 7/1998 | Thompson | ........... | A61M 25/10 604/264 |
| 6,029,671 A | 2/2000 | Stevens et al. | | |
| 6,090,096 A | 7/2000 | St. Goar et al. | | |
| 6,210,333 B1 * | 4/2001 | Gardner | ................ | A61B 8/481 600/450 |
| 6,458,323 B1 * | 10/2002 | Boekstegers | ....... | A61M 1/3621 422/44 |
| 6,500,145 B1 | 12/2002 | Bicakci et al. | | |
| 6,506,146 B1 | 1/2003 | Mohl et al. | | |
| 6,569,145 B1 * | 5/2003 | Shmulewitz | ..... | A61B 17/12022 604/102.01 |
| 6,669,624 B2 * | 12/2003 | Frazier | ................ | A61M 1/101 600/18 |
| 7,083,588 B1 * | 8/2006 | Shmulewitz | ........ | A61M 1/3613 604/8 |
| 7,159,592 B1 | 1/2007 | Makower et al. | | |
| 7,331,922 B2 * | 2/2008 | Mohl | ................ | A61M 1/1072 600/151 |
| 7,780,604 B2 * | 8/2010 | Mohl | ................ | A61M 1/1072 600/16 |
| 8,162,813 B2 * | 4/2012 | Mohl | ................ | A61B 17/12 600/17 |
| 8,177,704 B1 * | 5/2012 | Mohl | ................ | A61B 5/6859 600/16 |
| 8,262,580 B2 * | 9/2012 | Mohl | ................ | A61M 1/1072 600/16 |
| 8,267,887 B2 * | 9/2012 | Mohl | ............... | A61B 17/00234 604/102.01 |
| 8,444,598 B2 | 5/2013 | Doty | | |
| 8,540,618 B2 | 9/2013 | Kantrowski | | |
| 2001/0020160 A1 | 9/2001 | Esch et al. | | |
| 2001/0027287 A1 | 10/2001 | Shmulewitz et al. | | |
| 2001/0041863 A1 | 11/2001 | Sweezer | | |
| 2002/0062146 A1 | 5/2002 | Makower et al. | | |
| 2002/0120232 A1 | 8/2002 | Stumpp et al. | | |
| 2002/0155924 A1 | 10/2002 | Dardik | | |
| 2003/0032974 A1 | 2/2003 | Leschinsky | | |
| 2004/0172004 A1 | 9/2004 | Mohl | | |
| 2005/0015048 A1 * | 1/2005 | Chiu | ..................... | A61M 25/10 604/101.04 |
| 2005/0049451 A1 | 3/2005 | Schock | | |
| 2006/0074399 A1 | 4/2006 | Bates | | |
| 2006/0100639 A1 * | 5/2006 | Levin | ................. | A61M 25/1018 606/106 |
| 2007/0060883 A1 * | 3/2007 | Doty | ..................... | A61M 25/10 604/103.04 |
| 2008/0015404 A1 | 1/2008 | Mohl | | |
| 2008/0119742 A1 | 5/2008 | Mohl | | |
| 2008/0234658 A1 * | 9/2008 | Kassab | ..................... | A61F 2/07 604/508 |
| 2010/0056849 A1 | 3/2010 | Mohl | | |
| 2010/0130810 A1 | 5/2010 | Mohl | | |
| 2010/0211008 A1 | 8/2010 | Wiest | | |
| 2010/0256506 A1 * | 10/2010 | Mohl | .................. | A61B 5/0215 600/486 |
| 2011/0295301 A1 * | 12/2011 | Hoem | .................. | A61B 5/0215 606/194 |
| 2011/0295302 A1 * | 12/2011 | Mohl | ................. | A61B 17/1204 606/194 |
| 2012/0076690 A1 * | 3/2012 | Mohl | ............... | A61B 17/00234 422/45 |
| 2012/0076691 A1 * | 3/2012 | Mohl | ............... | A61B 17/00234 422/45 |
| 2012/0190913 A1 * | 7/2012 | Mohl | ..................... | A61B 17/12 600/17 |
| 2012/0245615 A1 * | 9/2012 | Mohl | .................. | A61M 1/1072 606/194 |
| 2012/0323065 A1 * | 12/2012 | Mohl | .................. | A61M 1/1072 600/17 |

OTHER PUBLICATIONS

Navia, Jose L., Firas Zahr, Kiyotaka Fukamachi, Mark Goodin, Paul Ragaller, Ji-Feng Chen, Michael W. Kopcak, Raymond Dessoffy, Yoshio Ootaki, Keiji Kamohara, Masatoshi Akiyama, Antonio Gutierrez, Jose A. Navia, Fernando Atik, and Delos M. Cosgrove.*

Mohl et al., "Intermittent Pressure Elevation of the Coronary Venous System as a Method to Protect Ischemic Myocardium," *Interactive CardioVascular and Thoracic Surgery*, vol. 4, 2005, pp. 66-69.

Syeda et al., "The Salvage Potential of Coronary Sinus Interventions: Meta-Analysis and Pathophysiologic Consequences," *The Journal of Thoracic and Cardiovascular Surgery*, vol. 127, No. 6 (Jun. 2004), pp. 1703-1712.

'Cannulation' [online]. Medtronic, Inc. 2010 [retrieved May 27, 2010]. Retrieved from the Internet: <URL: http://www.medtronic.com/for-healthcare-professionals/products-therapies/cardiovascular/therapies/cannulation/index.htm>.

'Cardioplegia Delivery' [online]. Quest Medical, Inc. 2010 [retrieved May 27, 2010]. Retrieved from the Internet: <URL: http://www.questmedical.com/products/cardio_catheters.asp>.

'Global Myocardial Protection' [online]. Edwards Lifesciences, 2004 [retrieved May 27, 2010]. Retrieved from the Internet: <URL: http://ht.edwards.com/resourcegallery/products/cannulae/images/ar00519.pdf>.

'Letters to the Editor: A New Technique for Pulmonary Arterial Catheter Insertion into Coronary Sinus Using Transesophageal

(56) References Cited

OTHER PUBLICATIONS

Echocardiography' [online]. International Anesthesia Research Society, 2003 [retrieved May 27, 2010]. Retrieved from the Internet: <URL: http://www.anesthesia-analgesia.org/content/97/1/298.full.pdf>.

'MiRCSP Cannulae' [online]. Medtronic, Inc. 2010 [retrieved May 27, 2010]. Retrieved from the Internet: <URL: http://www.medtronic.com/for-healthcare-professionals/products-therapies/cardiovascular/cannulae-products/mircsp-cannula/index.htm>.

'Myocardial Protection System' [online]. Quest Medical, Inc. 2010 [retrieved May 27, 2010]. Retrieved from the Internet: <URL: http://www.questmedical.com/products/mps.asp>.

'Performer CPB' [online]. Medtronic, Inc. 2007 [retrieved May 27, 2010]. Retrieved from the Internet: <URL: http://www.medtronic.com/cardsurgery/arrested_heart/downloads/200704933.pdf>.

'Retrograde Perfusion Cannulae' [online]. Medtronic, Inc. 2010 [retrieved May 27, 2010]. Retrieved from the Internet: <URL: http://www.medtronic.com/for-healthcare-professionals/products-therapies/cardiovascular/cannulae-products/retrograde-perfusion-cannulae/index.htm>.

Mohl, Werner et al. "Coronary Sinus Library, ICSO and PICSO" Society of Coronary Sinus Interventions, 2003. A. Holzhausens Nfg., Austria.

Mohl, Werner et al., "Is activation of coronary venous cells the key to cardiac regeneration?" Macmillan Publishers Ltd., 2008. Nature Clinical Practice, Cardiovascular Medicine, vol. 5, No. 9, pp. 528-530.

Mohl, Werner et al., "The legacy of coronary sinus interventions: Endogenous cardioprotection and regeneration beyond stem cell research." The American Association for Thoracic Surgery, 2008. The Journal of Thoracic and Cardiovascular Surgery, vol. 136, No. 5, pp. 1131-1135.

Onorati et al., "Coronary Sinus Perfusion Reverses Ongoing Myocardial Damage in Acute Ischemia." Wiley Periodicals, Inc. 2009. Journal compilation, International Center for Artificial Organs and Transplantation and Wiley Periodicals, Inc., 33 (10), pp. 788-797.

Mohl et al., "Reduction of Infarct Size Induced by Pressure-Controlled Intermittent Coronary Sinus Occlusion," The American Journal of Cardiology, Mar. 1984, 53: 923-928.

\* cited by examiner

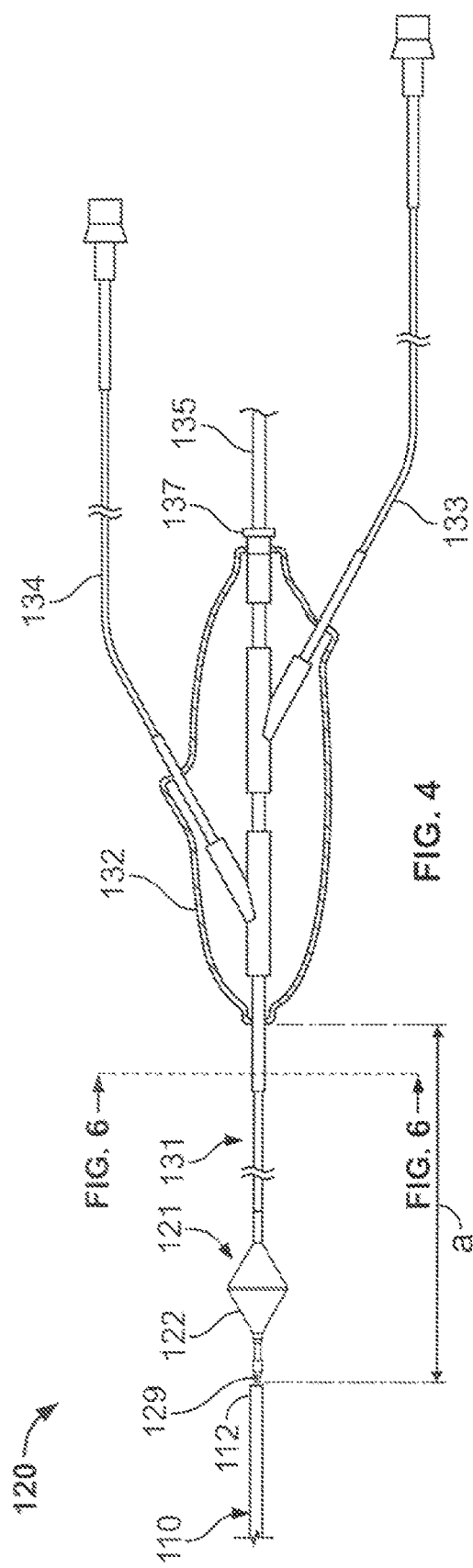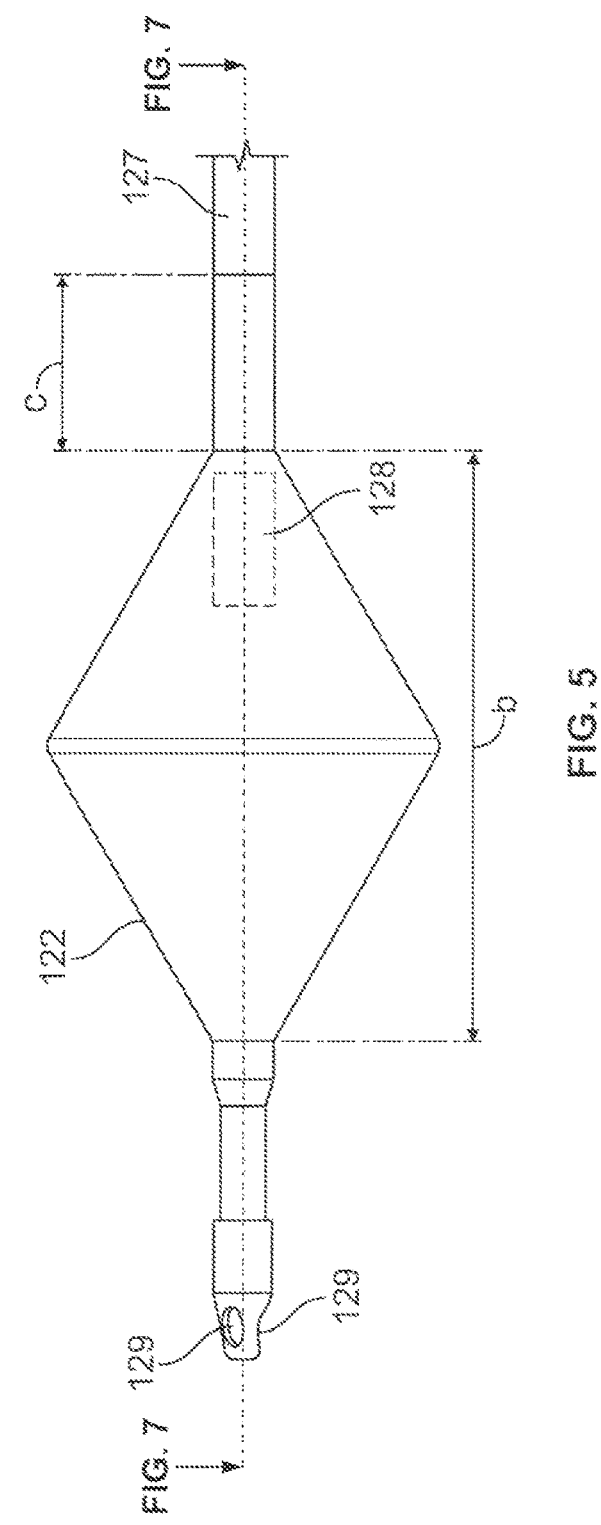

TREATING HEART TISSUE

CROSS-REFERENCE TO RELATED APPLICATION(S)

This application is a continuation of U.S. patent application Ser. No. 13/549,585 filed on Jul. 16, 2012, which is a division of U.S. patent application Ser. No. 12/786,785 filed on May 25, 2010 and entitled "Treating Heart Tissue." The entire contents of these previous applications are incorporated herein by reference.

TECHNICAL FIELD

This document relates to systems and methods that are configured to treat heart tissue, for example, to redistribute blood to damaged or ischemic heart muscle tissue.

BACKGROUND

The heart muscle receives arterial blood via coronary arteries so that the blood passes through and nourishes the heart muscle tissue. In some cases, a blockage in a coronary artery can result in a loss of blood flow through a portion of the heart muscle tissue, thereby creating an area of damaged or ischemic heart muscle tissue. After the blockage is removed or otherwise opened to resume blood flow, the ischemic portion of the heart muscle tissue (such as the reperfused microcirculation) may be damaged to point that normal blood flow does not return through the ischemic portion of the muscle tissue.

Some conventional systems attempt to repair or treat the ischemic heart muscle tissue by supplying the ischemic tissue with blood through retrograde perfusion. For example, the coronary sinus may be temporarily occluded so that the blood therein counterflows back from the coronary sinus through the coronary venous system and toward the ischemic muscle tissue that previously did not receive blood from the arterial side. The occlusion of the coronary sinus causes a pressure increase and, as a result, a redistribution of venous blood via the respective vein(s) into the capillaries of the border-zone ischemic muscle tissue so as to improve the supply of nutrients to that ischemic area. When the occlusion is ceased so that blood exits normally through the coronary sinus, the venous blood is flushed out while the metabolic waste products from the damaged tissue are carried off at the same time. The combination of venous pressure build-up with redistribution of flow and wash-out is believed to improve arterial blood demand and reduce ischemic tissue infarct size.

Typically, the instrument for occluding the coronary sinus is employed during or after treatment of the blockage in the coronary artery. Thus, a coronary intervention tool (e.g., stent, angioplasty balloon, or the like) would be used to treat the blockage on the coronary arterial system before making any attempt to temporarily occlude the coronary sinus of the coronary venous system.

SUMMARY

Some embodiments of a system or method for treating heart tissue enable a surgeon or other user to treat ischemic or otherwise damaged heart muscle tissue (e.g., caused by a coronary arterial blockage or other ailment) by redistributing venous blood flow to the damaged heart muscle tissue. In particular, the system and methods may be configured to pre-treat the heart tissue before any blockage in a coronary artery is repaired or removed. In these circumstances, the ischemic or otherwise damaged heart muscle tissue can receive a redistribution of blood flow from the coronary venous system (e.g., due to an instrument that temporarily occludes the coronary sinus) prior to the restoration of normal blood flow from the coronary arterial system. Such pre-treatment of the heart muscle tissue can lead to improved muscle tissue recovery after the coronary arterial blockage is treated and arterial blood flow returns to the previously blood-deprived portion of the heart muscle tissue.

In addition or in the alternative, some embodiments of the system for treating heart tissue can include a coronary sinus occlusion catheter having an inflatable balloon device and a control system to control the inflation and deflation of the inflatable balloon device. Preferably, the coronary sinus occlusion catheter can be activated to perform a pressure-controlled intermittent coronary sinus occlusion (PICSO) procedure for at least a portion of the time in which the catheter 120 is positioned in the coronary sinus of the heart. The control system can be equipped with a graphical user interface that provides a surgeon or other user with time-sensitive, relevant data indicative of the progress of PICSO procedure and the condition of the heart. As such, the user can readily monitor the patient's condition and the effects of the PICSO treatment by viewing the individual graphical user interface while contemporaneously handling the coronary sinus occlusion catheter other heart treatment instruments. In particular circumstances, the control system can be configured to activate the inflatable balloon device as part of a predetermined pattern of occlusion periods and release periods that is independent of the coronary sinus pressure or as part of a pressure-dependent pattern that is at least partially defined by the coronary sinus pressure readings during the procedure.

In some embodiments, a method of treating heart tissue may include detecting a blockage in a coronary artery of the heart. The method may also include prior to intervening on the blockage in the coronary artery, advancing distal tip portion of a coronary sinus occlusion catheter through a guide sheath in a right atrium and into the coronary sinus. The coronary sinus occlusion catheter may include an inflatable balloon device configured to occlude the coronary sinus when inflated. The method may further include intermittently occluding the coronary sinus using the inflatable balloon device of the coronary sinus occlusion catheter to redistribute venous blood flow into heart muscle tissue affected by the blockage. The method may also include after intermittently occluding the coronary sinus, delivering a coronary intervention tool via a body artery and to the blockage in the coronary artery of the heart to perform a coronary intervention procedure.

In particular embodiments, a method of treating heart tissue may include delivering a distal end of a guide member though a venous system and into a right atrium. The method may also include advancing a distal tip portion of a first coronary sinus occlusion catheter slidably along the guide member in the right atrium and into a coronary sinus. The first coronary sinus occlusion catheter may include an inflatable balloon device configured to occlude the coronary sinus when inflated. The method may further include intermittently occluding the coronary sinus using the inflatable balloon device of the first coronary sinus occlusion catheter to redistribute venous blood into heart muscle tissue affected by the blockage. The method may also include, after intermittently occluding the coronary sinus, withdrawing the first coronary sinus occlusion catheter from a proximal end of the guide member while the distal end of the guide member remains in the right atrium. The method may further include monitoring bodily characteristics for a period of time after the first coronary sinus occlusion catheter is withdrawn. The method may also include delivering a distal tip portion of a second coronary sinus occlusion catheter via the guide member remaining in the right atrium and into the coronary sinus. The second coronary sinus occlusion catheter may be different from first coronary sinus occlusion catheter.

In some embodiments, a system for treating heart muscle tissue may include a coronary sinus occlusion catheter including a distal tip portion, a proximal hub portion, a pressure sensor lumen, and a balloon fluid lumen. The distal tip portion of the coronary sinus occlusion catheter may include an inflatable balloon device configured to occlude a coronary sinus when inflated with fluid via the balloon fluid lumen. The system may also include a control system to control the inflation and deflation of the inflatable balloon device for pressure-controlled intermittent coronary sinus occlusion. The control system may include a display device, a pressure signal input that receives a pressure signal indicative of coronary sinus pressure, an electrocardiogram (ECG) signal input, and a control circuit that activates a pneumatic subsystem to inflate or deflate the inflatable balloon device of the coronary sinus occlusion catheter for a selected period of time based at least in part on the pressure signal indicative of the coronary sinus pressure. The control system, during an initial period of operation, may activate the inflatable balloon device of the coronary sinus occlusion catheter to intermittently occlude the coronary sinus in a predetermined pattern of occlusion periods and release periods that is independent of the pressure signal indicative of the coronary sinus pressure. Also, the control system, during a second period of operation, may activate the inflatable balloon device of the coronary occlusion catheter to intermittently occlude the coronary sinus in a pattern that is dependent in part on the pressure signal indicative of the coronary sinus pressure.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 is a cross-sectional view of a catheter device and a guide member of the system of FIG. 1.

FIG. 5 is a side view of a portion of the catheter device of FIG. 4.

Like reference symbols in the various drawings indicate like elements.

DETAILED DESCRIPTION

Figure 1:
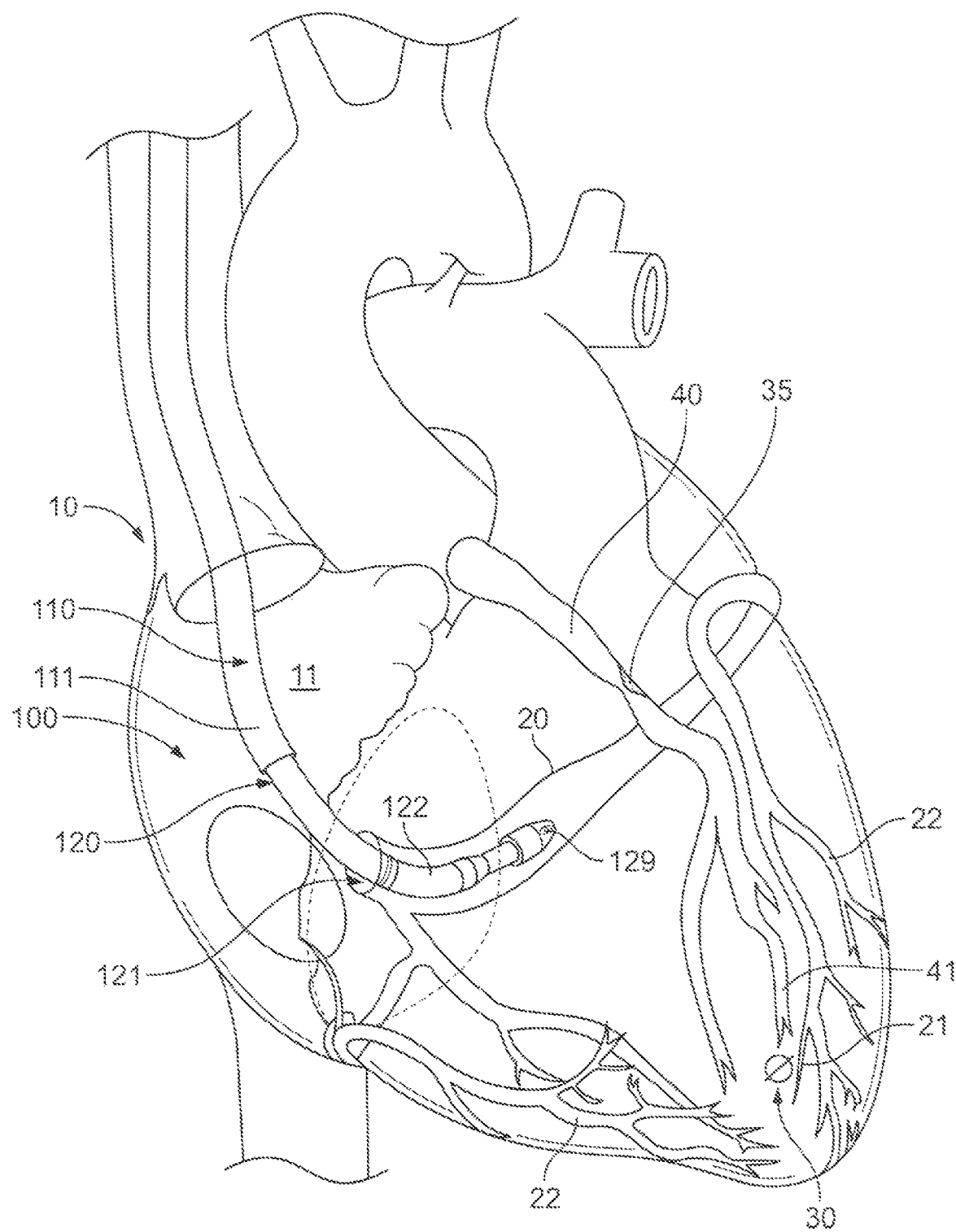
FIG. 1 is a perspective view of a portion of a system for treating heart tissue, in accordance with some embodiments.
Figure 2:
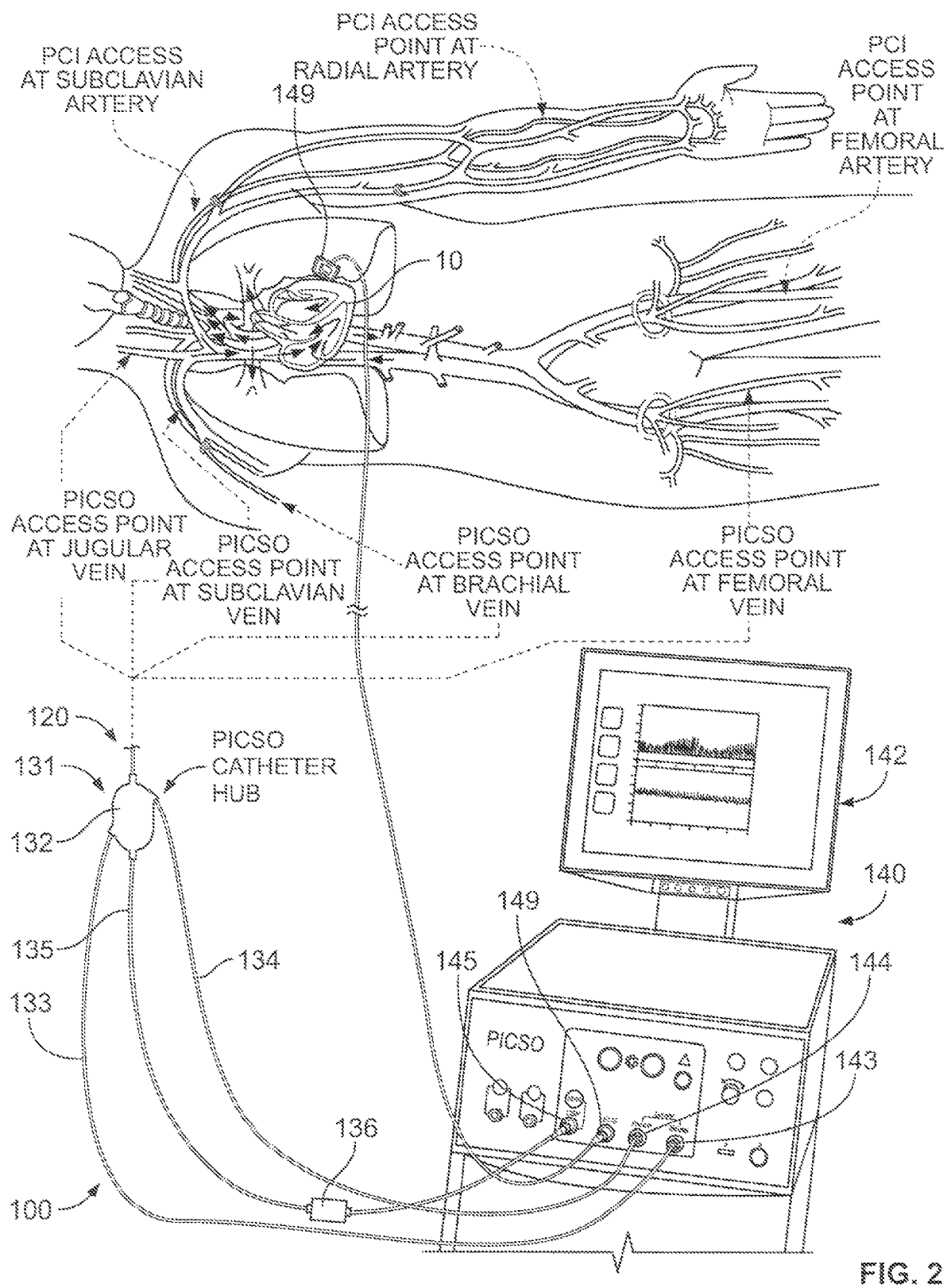
FIG. 2 is a perspective view of another portion of the system of FIG. 1.

Referring to FIGS. 1-2, some embodiments of a system 100 for treating heart tissue can include a coronary sinus occlusion catheter 120 and a control system 140 (FIG. 2). The control system 140 can be configured to control the operation of the catheter 120 for providing pressure-controlled intermittent coronary sinus occlusion (PICSO) and to receive heart sensor data for display. The coronary sinus occlusion catheter 120 includes a distal tip portion 121 (leading to a distal end depicted in FIG. 1) and a proximal portion 131, which includes a proximal hub 132 that is coupled to the control system 140 via a number of fluid or sensor lines 133, 134, and 135. Accordingly, the control system 140 may be employed to operate one or more components at the distal tip portion 121 of the coronary sinus occlusion catheter 120 while also receiving one or more sensor signals that provide data indicative of heart characteristics (e.g., coronary sinus pressure, electrocardiogram (ECG) information, and the like).

Briefly, in use, the distal tip portion 121 of the coronary sinus occlusion catheter 120 can be arranged in a coronary sinus 20 of a heart 10 and thereafter activated to intermittently occlude the blood flow exiting from the coronary sinus 20 and into the right atrium 11. During such an occlusion of the coronary sinus 20, the venous blood flow that is normally exiting from the coronary sinus 20 may be redistributed into a portion of heart muscle tissue 30 that has been damaged due to blood deprivation or loss of functional myocardium. For example, the portion of heart muscle tissue 30 can suffer from a lack of blood flow due to a blockage 35 in a coronary artery 40. As a result, the arterial blood flow to the affected heart muscle tissue 30 via a local artery 41 can be substantially reduced such that the heart muscle tissue 30 becomes ischemic or otherwise damaged. Further, because the arterial blood flow is reduced, the venous blood flow exiting from the local vein 21 is likewise reduced. Other branch veins 22 located at different regions along the heart 10 may continue to receive blood flow, thereby creating a supply of venous blood flow exiting through the coronary sinus 20. In some embodiments, the coronary sinus occlusion catheter 120 can be delivered into the coronary sinus 20 and thereafter activated so as to intermittently occlude the coronary sinus 20 prior to treating the blockage 35 on the arterial side. Such an occlusion can cause the venous blood flow to be redistributed to the local vein 21 and then into the portion of heart muscle tissue 30 can suffer from a lack of blood flow due to a blockage 35 in a coronary artery 40. As such, the ischemic or otherwise damaged heart muscle tissue 30 can be "pre-treated" with the redistributed venous blood flow in that the heart muscle tissue 30 receives an improved the supply of nutrients before the blockage 35 is repaired or removed to restore normal coronary arterial blood flow.

Furthermore, in use, the control system 140 (FIG. 2) is configured to provide automated control of an occlusion component (e.g., an inflatable balloon 122 or the like) of the coronary sinus occlusion catheter 120. As described in more detail below, the control system 140 includes a computer processor that executes computer-readable instructions stored on a computer memory device so as to activate or deactivate the occlusion in the coronary sinus 20 in accordance with particular patterns. For instance, the control system 140 can be configured to activate the occlusion component of the catheter 120 in the coronary sinus 20 as part of a predetermined pattern of occlusion periods and release periods that is independent of the coronary sinus pressure, or as part of a pressure-dependent pattern that is at least partially defined by the coronary sinus pressure readings during the procedure. In addition, the control system 120 is equipped with a display device 142 having a graphical user interface that provides a surgeon or other user with time-sensitive, relevant data indicative of the progress of a coronary sinus occlusion procedure and the condition of the heart 10. As such, the user can readily monitor the patient's condition and the effects of intermittently occluding the coronary sinus 20 by viewing the graphical user interface while contemporaneously handling the coronary sinus occlusion catheter 120 other heart treatment instruments (e.g., angioplasty catheters, stent delivery instruments, or the like). It is believed that a rapid change in coronary flow can be detected by observing the pressure in the occluded coronary sinus, thus indicating any detrimental change of nutritive flow. Likewise, an improvement of coronary flow can be detected using trend data (i.e., coronary sinus pressure measurements over a period of time). An abrupt increment of coronary flow (e.g., when a stent is inserted to reopen a coronary artery in acute coronary syndromes) can also be detected by an increment of pressure in the occluded coronary sinus. Furthermore, the pressure increase in the coronary sinus may also indicate a level of resistance in the ischemic tissue/reperfused microcirculation, thereby providing the cardiologist with an indication for the integrity of these vessels and the success of the percutaneous coronary interventional procedure.

It should be understood from the description herein that, in some embodiments, the control system 140 and the coronary sinus occlusion catheter 120 can be used as part of a system for "pre-treating" the heart muscle tissue before the blockage 35 is repaired or removed to restore normal coronary arterial blood flow (as previously described). In some alternative embodiments, the control system 140 and the coronary sinus occlusion catheter 120 can be used as part of a system that intermittently occludes the coronary sinus 20 after the blockage 35 is repaired or removed to restore normal coronary arterial blood flow.

Referring in more detail to FIG. 1, the coronary sinus occlusion catheter 120 can be delivered via the venous system to the coronary sinus 20 prior to repairing or treating the blockage 35 the coronary artery 40. In such circumstances, the portion of heart muscle tissue 30 that is damaged due to lack of arterial blood flow (as a result of the blockage) can be pre-treated with a supply of venous blood before the normal arterial blood flow is restored (as a result of repairing or removing the blockage 35). For example, as shown in FIG. 1, the distal tip portion 121 is delivered into the coronary sinus 20 for purposes of intermittently occluding the coronary sinus 20 before another catheter or instrument is advanced to the blockage 35 in the coronary artery 40.

The system 100 may include a guide member 110 that is advanced through the venous system of the patient and into the right atrium 11. The guide member 110 in this embodiment comprises a guide sheath having a lumen extending between a distal end 111 (FIG. 1) and a proximal end 112 (FIG. 4). In alternative embodiments, the guide member 110 can include a guide wire having an exterior surface extending between the distal end and the proximal end. Optionally, the guide member 110 includes a steerable mechanism to control the orientation of the distal end so as to steer the distal end 111 through the venous system and into the right atrium 11. Also, the guide member 110 can include one or more marker bands along the distal end 111 so that the position of the distal end can be monitored during advancement using an imaging device.

After the guide member 110 is advanced into the right atrium 11, the distal end 111 may be temporarily positioned in the coronary sinus 20. From there, the distal tip portion 121 of the coronary sinus occlusion catheter 120 can be slidably advanced along the guide member 110 for positioning inside the coronary sinus 20. In the embodiments in which the guide member 110 comprises a guide sheath, the distal tip portion 121 of the coronary sinus occlusion catheter 120 can slidably engage with an interior surface of the lumen during advancement toward the coronary sinus 20. In the alternative embodiments in which the guide member 110 comprises a guide wire structure, the distal tip portion 121 of the coronary sinus occlusion catheter 120 can slidably advance over the exterior surface of the guide wire (e.g., a lumen of the catheter 120 passes over the guide wire) during advancement toward the coronary sinus 20. After the coronary sinus occlusion catheter 120 reaches the coronary sinus 20, the distal end 111 of the guide member 110 can be withdrawn from the coronary sinus 20 and remain in the right atrium 11 during use of the coronary sinus occlusion catheter 120.

Still referring to FIG. 1, the distal tip portion 121 of the coronary sinus occlusion catheter 120 that is positioned in the coronary sinus 20 includes an occlusion component 122, which in this embodiment is in the form of an inflatable balloon device. The occlusion component 122 can be activated so as to occlude the coronary sinus 20 and thereby cause redistribution of the venous blood into the heart muscle tissue 30 that is damaged due to a lack of arterial blood flow. As described in more detail below, the inflatable balloon device 122 can be in fluid communication with an internal lumen of the coronary sinus occlusion catheter 120, which is in turn in communication with a pneumatic subsystem of the control system 140 (FIG. 2). As such, the control system 140 can be employed to expand or deflate the balloon device 122 in the coronary sinus.

The distal tip portion 121 also includes a one or more distal ports 129 that are positioned distally forward of the inflatable balloon device. In the depicted embodiments, the distal ports 129 face is a generally radially outward direction and are substantially uniformly spaced apart from one another along the circumference of the distal tip. As described in more detail below, the distal ports 129 may all be in fluid communication with a single pressure sensor lumen extending through the coronary sinus occlusion catheter 120. Accordingly, the coronary sinus pressure can be monitored via a pressure sensor device that is in fluid communication with the distal ports 129.

Further details of particular embodiments of the coronary sinus occlusion catheter 120 are described in more detail below in connection with FIGS. 4-7.

Referring now to FIG. 2, the proximal portion 131 of the coronary sinus occlusion catheter 120 and the control system 140 are positioned external to the patient while the distal tip portion 121 is advanced into the coronary sinus 20. The proximal portion 131 includes the proximal hub 132 that is coupled to the control system 140 via a set of fluid or sensor lines 133, 134, and 135. As such, the control system 140 can activate or deactivate the occlusion component 122 at the distal tip portion 121 of the coronary sinus occlusion catheter 120 while also receiving one or more sensor signals that provide data indicative of heart characteristics (e.g., coronary sinus pressure, electrocardiogram (ECG) information, and the like).

Figure 3:
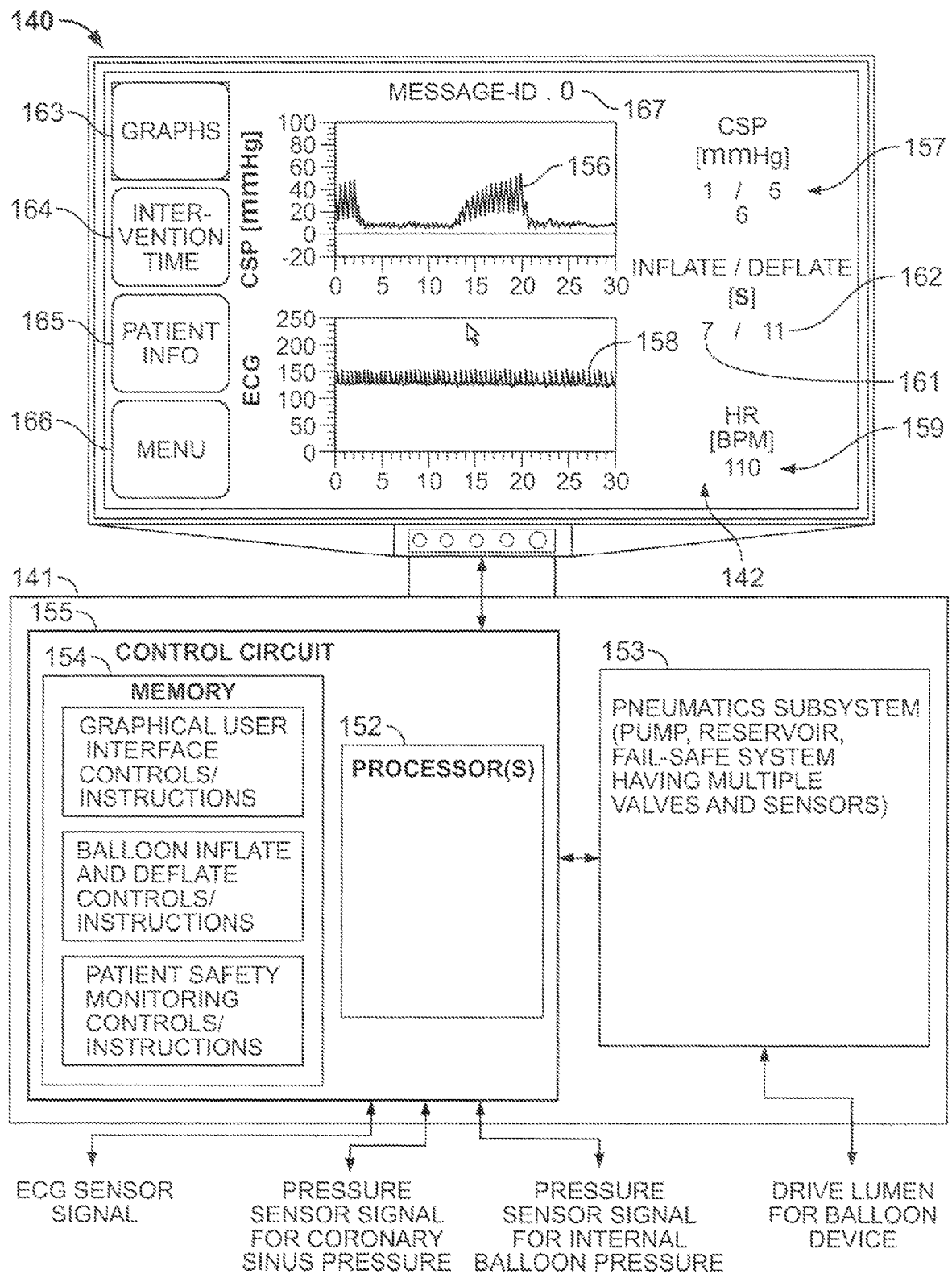
FIG. 3 is a diagram of a control system illustrated in the system of FIG. 2.

The proximal hub 132 of the coronary sinus occlusion catheter 120 serves to connect the plurality of fluid or sensor lines 133, 134, and 135 with the portion of the coronary sinus occlusion catheter 120 that extends into the patient's venous system. For example, the first line 133 extending between the control system 140 and the proximal hub 132 comprises a fluid line through which pressurized fluid (e.g., helium, another gas, or a stable liquid) can be delivered to activate the occlusion component (e.g., to inflate the inflatable balloon device 122). The fluid line 133 is connected to a corresponding port 143 of the control system 140 (e.g., the drive lumen port in this embodiment) so that the line 133 is in fluid communication with the pneumatic subsystem 153 housed in the control system 140 (as shown in FIG. 3). The proximal hub 132 joins the first line 133 with a balloon control lumen 123 (FIG. 6) extending through the coronary sinus occlusion catheter 120 and to the inflatable balloon device 122.

In another example, the second line 134 extending between the control system 140 and the proximal hub 132 comprises a balloon sensor line that is in fluid communication with the interior of the inflatable balloon device 122 so as to measure the fluid pressure within the balloon device 122. The proximal hub 132 joins the second line 134 with a balloon pressure lumen 124 (FIG. 6) extending through the coronary sinus occlusion catheter 120 and to the inflatable balloon device 122. The pressure of the balloon device 122 may be monitored by an internal control circuit 155 (FIG. 3) of the control system 140 as part of a safety feature that is employed to protect the coronary sinus 20 from an overly pressurized balloon device. The balloon sensor line 134 is connected to a corresponding port 144 of the control system 140 so that a pressure sensor arranged within the control system 140 can detect the fluid pressure in the balloon device 122. Alternatively, the pressure sensor may be arranged in the distal tip portion 121 or the in the proximal hub 132 such that only a sensor wire connects to the corresponding port 144 of the control system 140.

The proximal hub also connects with a third line 135 extending from the control system 140. The third line 135 comprises a coronary sinus pressure line that is used to measure the fluid pressure in the coronary sinus both when the balloon device 122 is inflated and when it is deflated. The proximal hub 132 joins the third line 135 with a coronary sinus pressure lumen 125 (FIGS. 5-6) extending through the coronary sinus occlusion catheter 120 and to the distal ports 129 that are forward of the balloon device 122. As such, the coronary sinus pressure lumen 125 and at least a portion of the third line 135 may operate as fluid-filled path (e.g., saline or another biocompatible liquid) that transfers the blood pressure in the coronary sinus 20 to pressure sensor device 136 along a proximal portion of the third line 135. The pressure sensor device 136 samples the pressure measurements (which are indicative of the coronary sinus pressure) and outputs an sensor signal indicative of the coronary sinus pressure to the corresponding port 145 of the controller system 140 for input to the internal control circuit 155 (FIG. 3). As described in more detail below, the coronary sinus pressure data are displayed by the graphical user interface 142 in a graph form 156 (refer to FIG. 3) so that a surgeon or other user can readily monitor the trend of the coronary sinus pressure while the coronary sinus 20 is in an occluded condition and in an non-occluded condition. Optionally, the graphical user interface 142 of the control system 140 can also output a numeric pressure measurement 157 (refer to FIG. 3) on the screen so that the surgeon can readily view a maximum coronary sinus pressure, a minimum coronary sinus pressure, or both. In alternative embodiments, the pressure sensor device 136 can be integrated into the housing 141 of the control system 140 so that the third line 135 is a fluid-filled path leading up to the corresponding port 145, where the internal pressure sensor device (much like the device 136) samples the pressure measurements and outputs a signal indicative of the coronary sinus pressure.

Still referring to FIG. 2, the system 100 may include one or more ECG sensors 149 to output ECG signals to the control system 140. In this embodiment, the system 100 includes a pair of ECG sensor pads 149 that are adhered to the patient's skin proximate to the heart 10. The ECG sensors 149 are connected to the control system 140 via a cable that mates with a corresponding port 149 along the housing of the control system 140. As described in more detail below, the ECG data are displayed by the graphical user interface 142 in a graph form 158 (refer to FIG. 3) so that a surgeon or other user can readily monitor the patient's heart rate and other characteristics while the coronary sinus is in an occluded condition and in an non-occluded condition. Optionally, the graphical user interface 142 of the control system 140 can also output numeric heart rate data 159 (refer to FIG. 3) (based on the ECG sensor data on the screen so that the surgeon can readily view the heart rate (e.g., in a unit of beats per minutes). The ECG sensor signals that are received by the control system 140 are also employed by the internal control circuit 155 (FIG. 3) so as to properly time the start of the occlusion period (e.g., the start time at which the balloon device 122 is inflated) and the start of the non-occlusion period (e.g., the start time at which the balloon device 122 is deflated).

As shown in FIG. 2, the coronary sinus occlusion catheter 120 is delivered to the heart 10 via a venous system using any one of a number of venous access points. Such access points may be referred to as PICSO access points in some embodiments in which the coronary sinus occlusion catheter 120 is controlled to perform a PICSO procedure for at least a portion of the time in which the catheter 120 is positioned in the coronary sinus 20. For example, the guide member 110 and the distal tip portion 121 can be inserted into the venous system into an access point at a brachial vein, an access point at a subclavian vein, or at an access point at a jugular vein. From any of these access points, the guide member 110 can be advanced through the superior vena cava and into the right atrium 11. Preferably, the guide member 110 is steered into an ostial portion of the coronary sinus 20, and then the distal tip portion 121 of the catheter 120 is slidably advanced along the guide member 110 and into the coronary sinus 20 before the guide member 110 is backed out to remain in the right atrium 11. In another example, the guide member 110 and the distal tip portion 121 can be inserted into the venous system into an access point at a femoral vein. In this example, the guide member 110 can be advanced through the inferior vena cava and into the right atrium 11. As previously described, the distal tip portion 121 of the catheter 120 is slidably advanced along the guide member 110 and into the coronary sinus 20 before the guide member 110 is backed out to remain in the right atrium 11.

In some embodiments, the coronary sinus occlusion catheter 120 is delivered to the coronary sinus 20 so as to pre-treat the heart tissue with redistributed venous blood flow before the blockage 35 in the coronary artery 40 is repaired or removed. In these circumstances, the damaged portion of heart muscle tissue 30 can receive a redistribution of blood flow from the coronary venous system (e.g., due to balloon device 122 that intermittently occludes the coronary sinus) prior to the restoration of normal blood flow from the coronary arterial system. Such pre-treatment of the heart muscle tissue can lead to improved muscle tissue recovery after the coronary arterial blockage is treated and arterial blood flow returns to the previously blood-deprived portion of the heart muscle tissue. In these embodiments, the coronary sinus occlusion catheter 120 can be delivered into the venous system (via one of the previously described PICSO access points illustrated in FIG. 2) before a different coronary intervention tool is delivered into the arterial system for purposes of repairing or removing the blockage 35. For example, the blockage 35 may be repaired or removed using a percutaneous coronary intervention (PCI) instrument such as an angioplasty balloon catheter, a stent delivery instrument, or the like. The PCI instrument may access the arterial system via any one of a number of PCI access points. In some implementations, the PCI instrument can be inserted into the arterial system into an access point at a femoral artery, an access point at a radial artery, or an access point at a subclavian artery. Thus, as previously described, some embodiments of the system 100 may employ a PICSO access point into the venous system prior to a PCI access point is employed to insert a PCI instrument into the arterial system.

Referring now to FIG. 3, some embodiments of the control system 140 include the internal control circuit subsystem 155 that communicates with the pneumatics subsystem 153. The control circuit subsystem 155 can include one or more processors 152 that are configured to execute various software modules stored on at least one memory device 154. The processors 152 may include, for example, microprocessors that are arranged on a motherboard so as to execute the control instructions of the control system 140. The memory device 154 may include, for example, a computer hard drive device having one or more discs, a RAM memory device, that stored the various software modules.

In some embodiments, the memory device of the control circuit subsystem 155 stores a graphical user interface software module including computer-readable instructions for controlling the graphical user interface 142. These graphical user interface control instructions may be configured to cause the interface 142 (which includes a touch screen display device in this embodiment) to display: the pressure data graph 156 indicative of the coronary sinus pressure, the coronary sinus pressure numerical data 157, the ECG data graph 158, and the heart rate numerical data 159 (previously described in connection with FIG. 2). Optionally, the graphical user interface can be configured to display more than two the two graphs 157 and 158 on the screen. For example, in some embodiments, the graphical user interface can be configured to contemporaneously display three or four different graphs, such as the coronary sinus pressure numerical data 157, the ECG data graph 158, a third graph that depicts the arterial pressure as a function of time, and a fourth graph that illustrates another data output (e.g., the volume of blood flow).

Further, the graphical user interface control instructions stored in the control circuit subsystem 155 may be configured to cause the interface 142 to display numeric data of the time periods during which the coronary sinus is in an occluded state and in a non-occluded state. For example, the graphical user interface 142 can provide the occluded time numeric data 161 in units of seconds (e.g., 7 seconds as shown in FIG. 3). Also, the graphical user interface 142 can provide the non-occluded time numeric data 162 in units of seconds (e.g., 11 seconds as shown in FIG. 3). The calculation of the time periods during which the coronary sinus is in an occluded state and in a non-occluded state may be completed by the balloon inflate and deflate software module stored on the memory device 154, as described in more detail below. This software module can be configured to determine a time derivative of the coronary sinus pressure curve over time during PICSO, which can be employed as a parameter in determining the balloon inflate and deflate times. The graphical user interface control instructions stored in the control circuit subsystem 155 may be configured to cause the interface 142 to display a number of touch screen buttons 163, 164, 165, and 166 that enable the surgeon or other user to select different menu options or to input patient information or other data. In addition, the graphical user interface control instructions stored in the control circuit subsystem 155 may be configured to cause the interface 142 to display a number of one or more alerts 167, which can be in the form of error messages or codes. The determination of which alert condition, if any, should be display is completed by the patient safety monitoring software module stored on the memory device 154, as described in more detail below.

Still referring to FIG. 3, the balloon inflate and deflate software module stored on the memory device 154 can include computer-readable instructions that, when executed by one of the processors 152 (such as an embedded microprocessor), causes the pneumatic subsystem 153 to activate or deactivate the balloon device 122 at selected times. In some embodiments, the balloon inflate and deflate software module stored on the memory device 154 can implement a customized algorithm that calculates and updates the time periods during which the coronary sinus is in an occluded state and in a non-occluded state based upon the coronary sinus pressure measurements. In such circumstances, the coronary sinus 20 is not occluded and non-occluded according to a predetermined pattern of inflated times and deflated times that are independent of the patient, but instead the coronary sinus pressure measurements at least partially dictate the time periods during which the coronary sinus is in an occluded state and in a non-occluded state. In alternative modes, the balloon inflate and deflate software module stored on the memory device 154 may cause the coronary sinus 20 to be occluded and non-occluded according to a predetermined pattern of inflated times and deflated times that are independent of the patient and the coronary sinus pressure measurements. For example, as described in more detail below, the control circuit subsystem 154 may execute the balloon inflate and deflate software module and communicate with the pneumatic subsystem 153 to inflate and deflate the balloon device 122 according to the predetermined pattern of inflated times and deflated times during an initial phase when the catheter 120 is first delivered into the coronary sinus 20 and initially activated. After this initial phase during which the coronary sinus pressure measurements are sampled and displayed, the control circuit subsystem 154 may execute the balloon inflate and deflate software module and communicate with the pneumatic subsystem 153 so as to inflate and deflate the balloon device 122 according to the customized algorithm that is dependent upon the coronary sinus pressure measurements in the patient (e.g., a PICSO procedure in which the intermittent occlusion of the coronary sinus is pressure-controlled).

After this second phase during which the pneumatic subsystem 153 inflates and deflate the balloon device 122 according to the customized algorithm that is dependent upon the coronary sinus pressure measurements in the patient, the control circuit subsystem 154 may execute the balloon inflate and deflate software module during a third phase that again uses the predetermined pattern of inflated times and deflated times that are independent of the patient and the coronary pressure measurements. Because this predetermined pattern of occlusion periods and release periods from the first (initial) phase is repeated during the third phase, the coronary sinus pressure readings from these two different phases can be compared. For example, the coronary sinus pressure measurements during this third phase (having the predetermined pattern of occlusion and non-occlusion) is used to compare with the previous coronary sinus pressure measurements during the earlier first phase (having the predetermined pattern of occlusion and non-occlusion). The comparison can be displayed by the control system 140 so that the surgeon or other user can determine if the intermittent coronary sinus occlusion procedure has reached its clinical efficacy end-point or if further delivery of the coronary sinus occlusion treatment is required. In some cases, the cardiologist can observe the trend data (e.g., the coronary sinus pressure curve that increased toward a plateau level) to determine if clinical stability is reached (e.g., when the trend flattens).

The patient safety monitoring software module stored on the memory device 154 can include computer-readable instructions that, when executed by one of the processors 152, causes the control circuit subsystem 155 to detect if any of the system sensors (e.g., the pressure sensors) output a measurement that is outside of a selected safety range. For example, if the coronary sinus pressure signal input to the control system 140 indicates a coronary sinus pressure that is above a selected threshold, the control circuit subsystem 155 can cause the graphical user interface 142 to display an alert 167 in the form of a textual message or an error code. Further, in some embodiments, the control circuit subsystem 155 may automatically cause the pneumatic subsystem to deflate the balloon device 122 so as to immediately reduce the high pressure in the coronary sinus 20.

Still referring to FIG. 3, the pneumatic subsystem 153 of the control system 140 can be configured to promptly inflate or deflate the balloon device 122 in response to the control circuit subsystem. In some embodiments, the pneumatic subsystem may include a reservoir containing pressurized gas, such as helium, and a vacuum pump. The reservoir and the vacuum pump can be controlled by a set of valves and are monitored by a set of pressure sensors that feedback into the control circuit subsystem 155. In such circumstances, the pneumatic subsystem can be configured to inflate or deflate the balloon device 122 at the distal tip portion 121 of the coronary sinus occlusion catheter 120 in less than 1 second, less that about 0.6 seconds, and preferably less than about 0.4 seconds.

Referring now to FIGS. 4-7, the coronary sinus occlusion catheter 120 carries the inflatable balloon device 122 along its distal tip portion 121 while the proximal hub 132 is arranged along the proximal portion 131. As previously described, the proximal hub 132 serves as the connection interface between the fluid or sensor lines 133, 134, and 135 (FIG. 4) and the corresponding lumens 123, 124, and 125 (FIG. 6) extending through the catheter 120. In this embodiment depicted in FIG. 4, the coronary sinus pressure sensor line 135 is connected to the proximal hub 132 using a Luer lock 137 so as to maintain the fluid path from the central lumen 125 of the catheter 120 to the lumen of the line 135. In some embodiments, the hub-to-tip distance (length "a" shown in FIG. 4) can be selected to enable the catheter 120 to be introduced both via the access point at the jugular vein (FIG. 2) and via access point at the femoral vein (FIG. 2).

As previously described, the system 100 may include a guide member 110 that is used to direct the coronary sinus occlusion catheter 120 through the venous system and into the heart 10. Referring to FIG. 4, the guide member 110 may be a guide sheath having a central lumen extending from a proximal end 112 (FIG. 4) to a distal end 111 (FIG. 1.) As previously described, the guide member 110 may be equipped with a steering mechanism (e.g., steel cables, a shape memory element, or the like) so that the surgeon can more readily advance the guide member 110 through the venous system and into the right atrium.

Still referring to FIGS. 4-7, the inflatable balloon device 122 of the coronary sinus occlusion catheter 120 may have a predetermined shape when in the inflated condition. In this embodiment, the inflatable balloon device 122 includes a first conical portion narrowing down toward the distal direction, a second conical portion narrowing down toward the proximal direction, and a small generally cylindrical rim portion which is arranged between the conical portions. The narrowed ends of each of the conical portions are connected with the catheter shaft so as to provide a seal that prevents gas leakage from the balloon device 122. In the inflated condition, the diameter of the balloon device 122 in the region of the cylindrical rim portion is, for example, between about 12 mm and about 22 mm, and preferably about 15 mm. The length "b" of the balloon device is, for example, between about 20 mm and about 30 mm, and preferably about 25 mm. As shown in FIG. 5, the coronary sinus occlusion catheter 120 can be equipped with a marker band 128 (positioned inside the balloon device 122 in this embodiment) that comprises an X-ray compatible material so as to be rendered visible during a surgery by suitable imaging processes.

Figure 6:
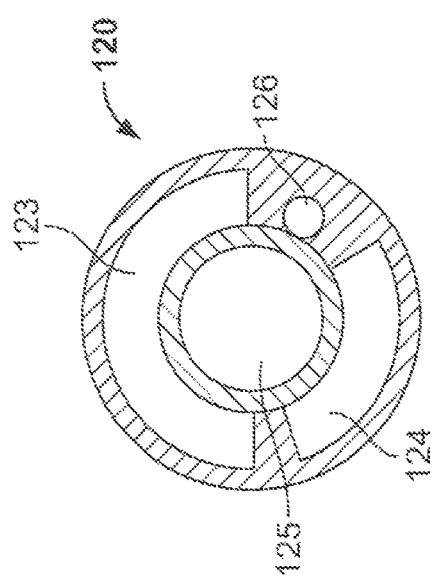
FIG. 6 is a cross-sectional view of a shaft portion the catheter device of FIG. 4.

As shown in FIG. 6, the shaft of the coronary sinus occlusion catheter 120 extending distally from the proximal hub 132 can include a plurality of lumens 123, 124, 125, and 126. In this embodiment, the ring segment-shaped lumen 123 serves to supply and discharge fluid (e.g., helium gas in this embodiment) for inflating and evacuating the balloon device 122. The ring segment-shaped lumen 124, which is smaller than the other lumen 123, likewise communicates with the interior of the balloon device 122 and serves to measure the fluid pressure within the balloon device 122. The central lumen 125 in this embodiment is employed for measuring the coronary sinus pressure. The central lumen 125 is in fluid communication with the distal ports 129 of the catheter 120 so that the blood pressure in the coronary sinus is transferred to the fluid-filled path extending through the central lumen 125 and to the pressure sensor device 136 (FIG. 2). Alternatively, a miniature pressure sensor can be positioned immediate adjacent to the distal ports 129 such that a sensor wire (e.g., electrical or optical) extends through the central lumen 125 for communication with the control system 140 (FIG. 2). In this embodiment, the shaft of the coronary sinus occlusion catheter 120 includes a fourth lumen 126 having a circular cross section. One or more additional sensors or sensor wires can be positioned in this fourth lumen. Alternatively, a stiffening wire can be arranged in the fourth lumen 126 so as to extend through the catheter shaft in the region of the balloon device 122. The stiffening wire, which can comprise of a shape memory material such as Nitinol, can be used to facilitate delivery of the distal tip portion 121 into the coronary sinus 20.

Figure 7:
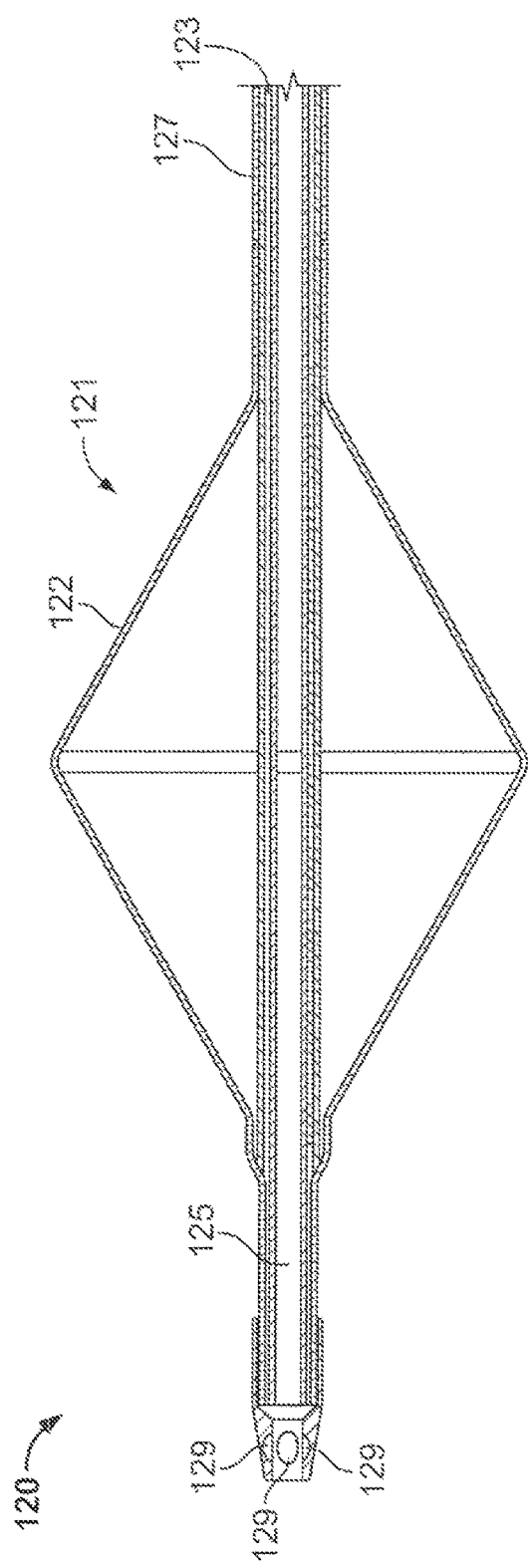
FIG. 7 is a cross-sectional view of a tip portion the catheter device of FIG. 4.

Referring to FIGS. 5 and 7, the distal ports 129 of the catheter 120 are arranged distally forward of the balloon device 122 and are oriented to face generally radially outward (e.g., not facing axially outward from the end of the catheter 120). This tip portion of the coronary sinus occlusion catheter 120 can be configured so that the fluid pressure in the coronary sinus can be accurately measured even if a portion of the distal end abuts against a wall of the coronary sinus. In this embodiment, the distal ports 129 comprise three ports that are evenly spaced apart along the circumference of the tip (which has a slightly conical barrel), thereby enabling the fluid pressure in the coronary sinus to be applied into one or more the ports 129 even if one side of the tip is pressed against a wall of the coronary sinus.

Optionally, a hypotube 127 can surround at least a portion the catheter shaft so as to permit the distal tip portion 121 of the catheter 120 to follow the curvatures of the venous system during delivery to the heart 10. As shown in FIGS. 5 and 7, a hypotube 127 can surround at least a portion the catheter shaft at a distance "c" from the proximal end of the balloon device 122. The hypotube 127 may comprise a helical line-shaped notch formed along its periphery, and the pitch of the helix at the distal portion of the hypotube 127 can be smaller than in a more proximally located region. This results in a reduced flexural strength in the distal portion of the hypotube 127 so as to enable the catheter to follow the curvatures of the venous system during delivery to the heart 10.

Figure 8:
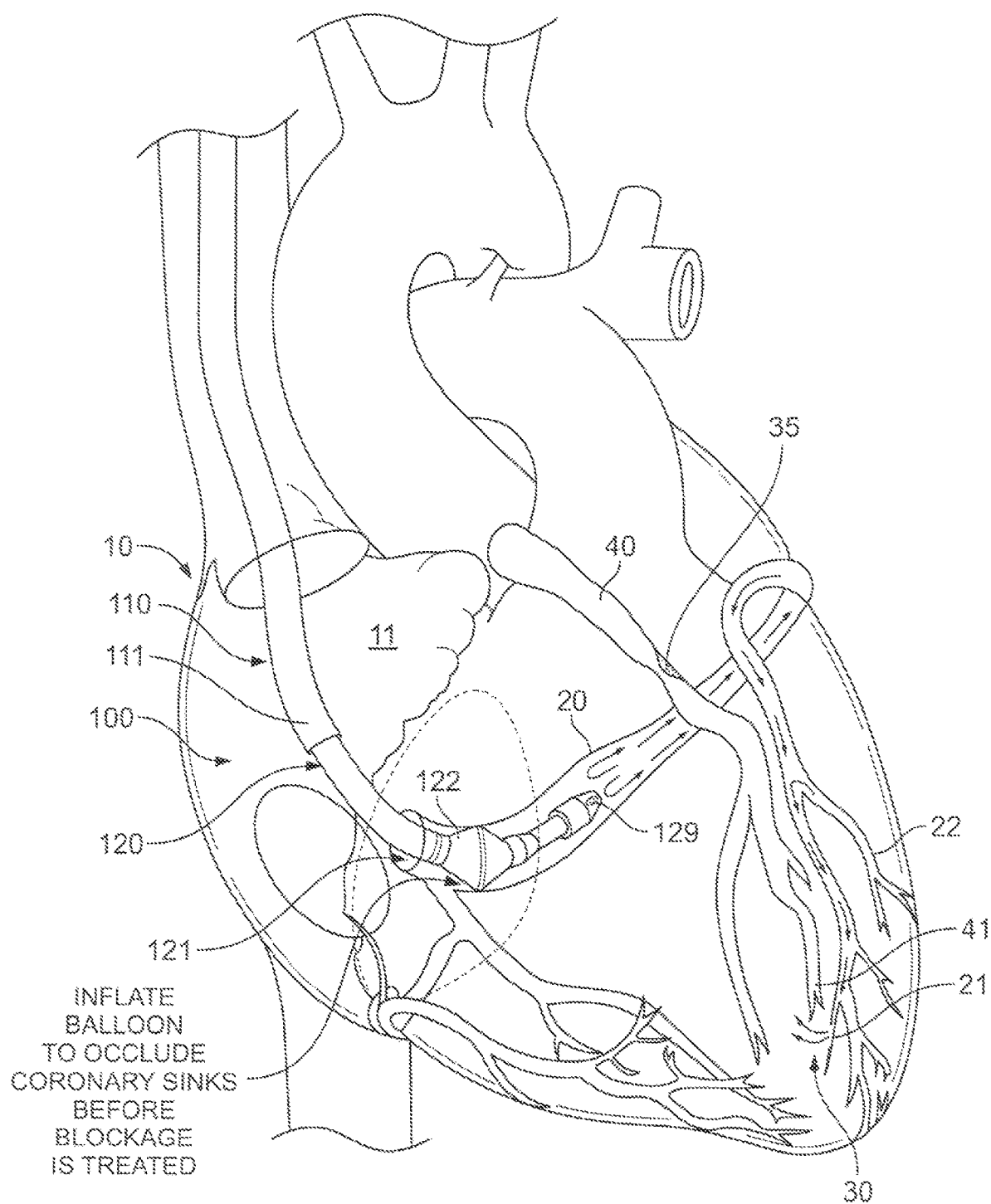
FIG. 8 is a perspective view of the catheter device and the guide member of the system of FIG. 1, with the tip portion of the catheter device being arranged in a coronary sinus of a heart.
Figure 9:
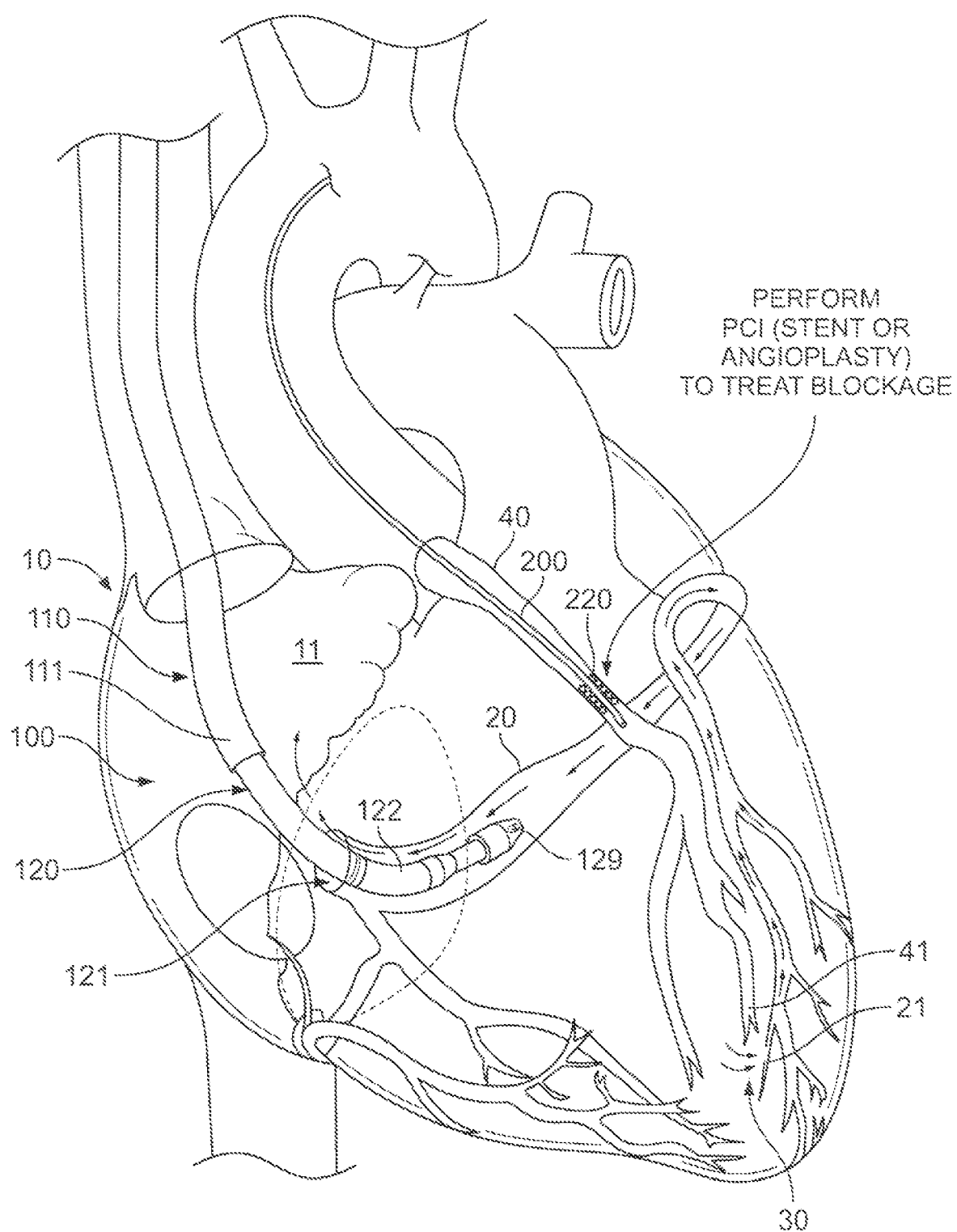
FIG. 9 is a perspective view of the catheter device and the guide member of FIG. 8, with a coronary intervention tool arranged in a coronary artery.
Figure 10:
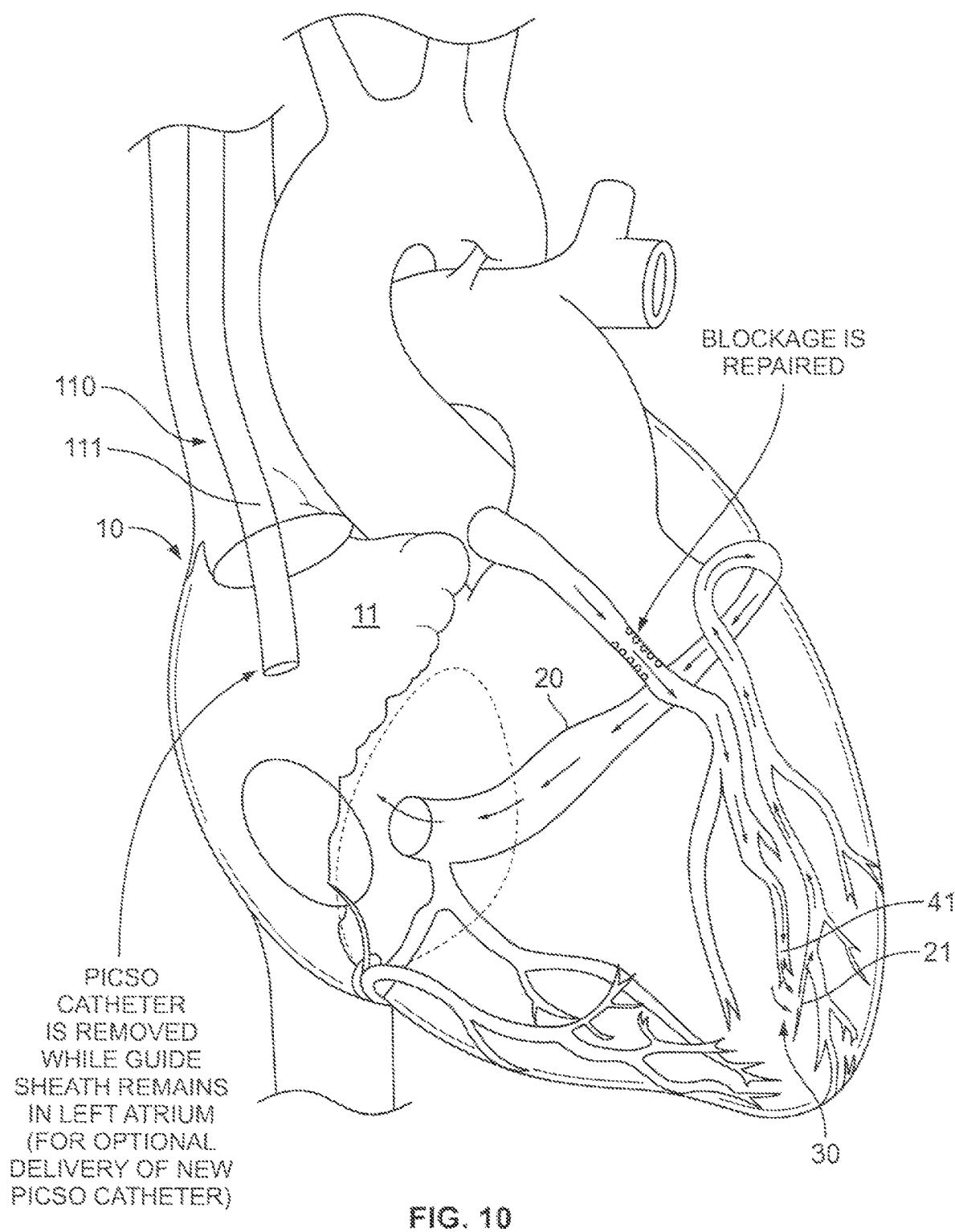
FIG. 10 is a perspective view of the guide member of FIG. 8, with the catheter device being withdrawn.

Referring now to FIGS. 8-10, the system 100 previously described in connection with FIGS. 1-2 can be configured to pre-treat damaged heart muscle tissue with redistributed venous blood flow before coronary artery blockage 35 repaired or removed. While FIGS. 8-10 depicted some embodiments of using the system 100 to treat the heart muscle tissue, it should be understood from the description herein that the system 100 can also be employed in alternative procedures where the coronary sinus occlusion catheter 120 does not redistribute the coronary venous blood flow until after the coronary artery blockage 35 is initially accessed for repair or removal.

As shown in FIG. 8, the distal tip portion 121 of the coronary sinus occlusion catheter 120 can be arranged in the coronary sinus 20 and thereafter activated to occlude the blood flow exiting from the coronary sinus 20 and into the right atrium 11. As previously describe din connection with FIG. 1, the coronary sinus occlusion catheter 120 can be delivered via the venous system to the coronary sinus 20 prior to repairing or treating the blockage 35 the coronary artery 40. When the inflatable balloon device 122 of the catheter 120 occludes the coronary sinus, the portion of heart muscle tissue 30 that is damaged due to lack of arterial blood flow (as a result of the blockage) can be pre-treated with a supply of venous blood before the normal arterial blood flow is restored (as a result of repairing or removing the blockage 35). In particular, the venous blood flow that is normally exiting from the coronary sinus 20 will be redistributed into the portion of heart muscle tissue 30 that has been damaged due to blood deprivation via the local artery 41.

During the period of occlusion of the coronary sinus 20, other branch veins 22 located at different regions along the heart 10 may continue to receive blood flow, thereby creating a supply of venous blood flow attempting to exit through the coronary sinus 20. Because the exit from the coronary sinus 20 is occluded by the balloon device 122, the venous blood flow from the other veins 22 is redistributed to the local vein 21 and then into the portion of heart muscle tissue 30 that is suffering from a lack of blood flow due to the blockage 35 in the coronary artery 40. This redistributed venous blood flow in the coronary venous system causes the ischemic or otherwise damaged heart muscle tissue 30 to be pre-treated with an improved the supply of nutrients before the blockage 35 is repaired or removed to restore normal coronary arterial blood flow.

Still referring to FIG. 8, the inflatable balloon device 122 of the coronary sinus occlusion catheter 120 can be intermittently inflated and deflated so as to cause the previously described redistribution of venous blood flow while also preventing the pressure in the coronary sinus from reaching unsafe levels. In particular embodiments, the control system 140 (FIGS. 2-3) can activate and deactivate the balloon device 122 (causing inflation and deflation) according to one of two types of operations: (1) a predetermined pattern of intermittent coronary sinus occlusion (time periods are independent of coronary sinus pressure measurements), or (2) a pressure-controlled intermittent coronary sinus occlusion (time periods are dependent upon the coronary sinus pressure measurements). For example, during an initial phase when the catheter 120 is first delivered into the coronary sinus 20 and initially activated, the control system 140 can inflate and deflate the balloon device 122 according to the predetermined pattern of inflated times and deflated times. One example of the predetermined pattern may be:

7 seconds of occluded state (balloon device 122 inflated),
3 seconds of non-occluded state (balloon device 122 deflated),
10 seconds of occluded state,
4 seconds of non-occluded state,
12 seconds of occluded state,
3 seconds of non-occluded state,
6 seconds of occluded state,
3 seconds of non-occluded state,
20 seconds of occluded state,
5 seconds of non-occluded state,
14 seconds of occluded state,
3 seconds of non-occluded state,
7 seconds of occluded state,
3 seconds of non-occluded state,
16 seconds of occluded state,
3 seconds of non-occluded state,
10 seconds of occluded state, and
4 seconds of non-occluded state.

During these time periods in the initial phase, the coronary sinus pressure measurements are recorded by the control system 140 (and displayed on the user interface 142), but the time periods for the occluded state and the non-occluded state are predetermined and do not changed based upon the coronary sinus pressure measurements. These time periods of occlusion and non-occlusion in the initial phase are used gather coronary sinus pressure data, which allows comparisons of the pressure curve at different times and permits the control system 140 to adjust or optimize a cycle length during the next phase (pressure-controlled coronary sinus occlusion). In some cases, the control system 140 repeats the predetermined pattern of occlusion periods and release periods so as to provide a quantitative estimated of changes within the treated heart.

After this initial phase, the control system 140 can automatically switch the second type of operation in which the time periods for the occluded state and the non-occluded state are a function of the previously recorded coronary sinus pressure measurements. For example, the control system 140 can inflate and deflate the balloon device 122 according to the previously described algorithm that assesses a previous set of coronary sinus pressure measurements in a function that estimates the new time period for the next occluded state or non-occluded state.

Referring now to FIG. 9, when the balloon device 122 of the coronary sinus occlusion catheter 120 is in a deflated condition, the coronary sinus 20 is not occluded and the venous blood flow can resumes its normal path to exit fro the coronary sinus 20 into the right atrium. The blood that was previously redistributed to the damaged portion of the heart tissue 30 can also pass through the venous system and exit out of the coronary sinus 20. While the venous blood is flushed out of the damaged tissue 30, at least some portion of the metabolic waste products from the damaged tissue 30 can be carried off at the same time, thereby helping to reduce or eliminate the ischemic tissue infarct size.

As shown in the embodiment in FIG. 9, after the coronary sinus occlusion catheter 120 intermittently occludes the coronary sinus 20 (e.g., intermittently adjusts between the inflated condition in FIG. 8 and the deflated condition in FIG. 9) to pre-treat the damaged heart tissue 30, a different instrument 200 can be advanced into the coronary artery 40 toward the blockage 35. The blockage treatment instrument 200 can be a percutaneous coronary intervention (PCI) instrument, such as an angioplasty balloon catheter or a stent delivery instrument. In this embodiment, the PCI instrument 200 is in the form of stent delivery instrument which carries a stent device 220 along a distal portion for purposes of treating the blockage 35 in the coronary artery 40. When the stent device 220 reaches the blockage 35, the stent device 220 can expand to widen the artery and remove the blockage 35 that disrupted arterial blood flow to the local artery 41 near the damaged heart muscle tissue 30.

It should be understood from the description herein that, in some embodiments, the coronary sinus occlusion catheter 120 may continue to intermittently occlude the coronary sinus (as shown in FIG. 8) during use of the second instrument 200 to treat the arterial blockage 35. In such circumstances, the balloon device 122 of the coronary sinus occlusion catheter 120 can intermittently occlude the coronary sinus 20 and thereby redistribute the venous blood flow to the damaged portion of the heart muscle tissue 30. Further, in some embodiments, the coronary sinus occlusion catheter 120 may continue to intermittently occlude the coronary sinus (as shown in FIG. 8) even after the second instrument 200 has completed the procedure to repair or remove the arterial blockage 35. The duration of time for using the coronary sinus occlusion catheter 120 to intermittently occlude the coronary sinus 20 may be determined by the surgeon based upon a number of factors, including the trend of the coronary sinus pressure measurements (as displayed on the user interface 142), a measurement of particular bio-markers present in the patient's blood (e.g., lactate (which increases in the event of ischemia), potassium (an indicator of ischemic tissue), and the like).

Referring now to FIG. 10, the coronary sinus occlusion catheter 120 can be removed from the heart 10 some time after the blockage treatment device 200 is employed to repair the blockage in the coronary artery 40. In circumstances, the guide member 110 can remain in the right atrium while the coronary sinus occlusion catheter 120 is removed. In this embodiment, the guide member 110 comprises a guide sheath, so the internal lumen of the guide sheath 110 may be subject to continued flushing after the coronary sinus occlusion catheter 120 is fully removed from the proximal portion of the guide sheath 110 outside the patient's body. As described in more detail below, the guide sheath 110 may remain in the right atrium during a post-treatment monitoring period after the coronary sinus occlusion catheter 120 is removed so as to provide simplified access in the event that a new coronary sinus occlusion catheter 120 is required.

For example, after the blockage is repaired (FIG. 9) and the coronary sinus occlusion catheter 120 is withdrawn from the body (FIG. 10), the patient's recovery may be closely monitored for a period of minutes or hours (e.g., about one to about six hours) to determine if additional intermittent coronary sinus occlusion treatment is warranted. During this period, the patient's biomarkers (e.g., lactate, potassium, and the like) and ECG data can be monitored to determine if the heart's condition is improving or if additional treatment with a new coronary sinus occlusion catheter 120 is required to treat damaged heart muscle tissue. If, during this post-treatment monitoring period, the patent's heart condition improves toward a satisfactory recovery, then the guide sheath 110 can be removed from the right atrium 11. If, during this post-treatment monitoring period, the patent's heart condition indicates that additional treatment is required using a new coronary sinus occlusion catheter 120, the new catheter 120 can be promptly advanced through the guide sheath 111 (which was previously employed with the first coronary sinus occlusion catheter 120) and into the coronary sinus as shown in FIG. 1. In one example, the new coronary sinus occlusion catheter can be employed to perform pressure-controlled coronary sinus occlusion treatment for a period time in an effort to limit or repair reperfusion damage as well as to establish pathways for recovery (e.g., limiting inflammation and inducing regeneration of microcirculation).

Figure 11:
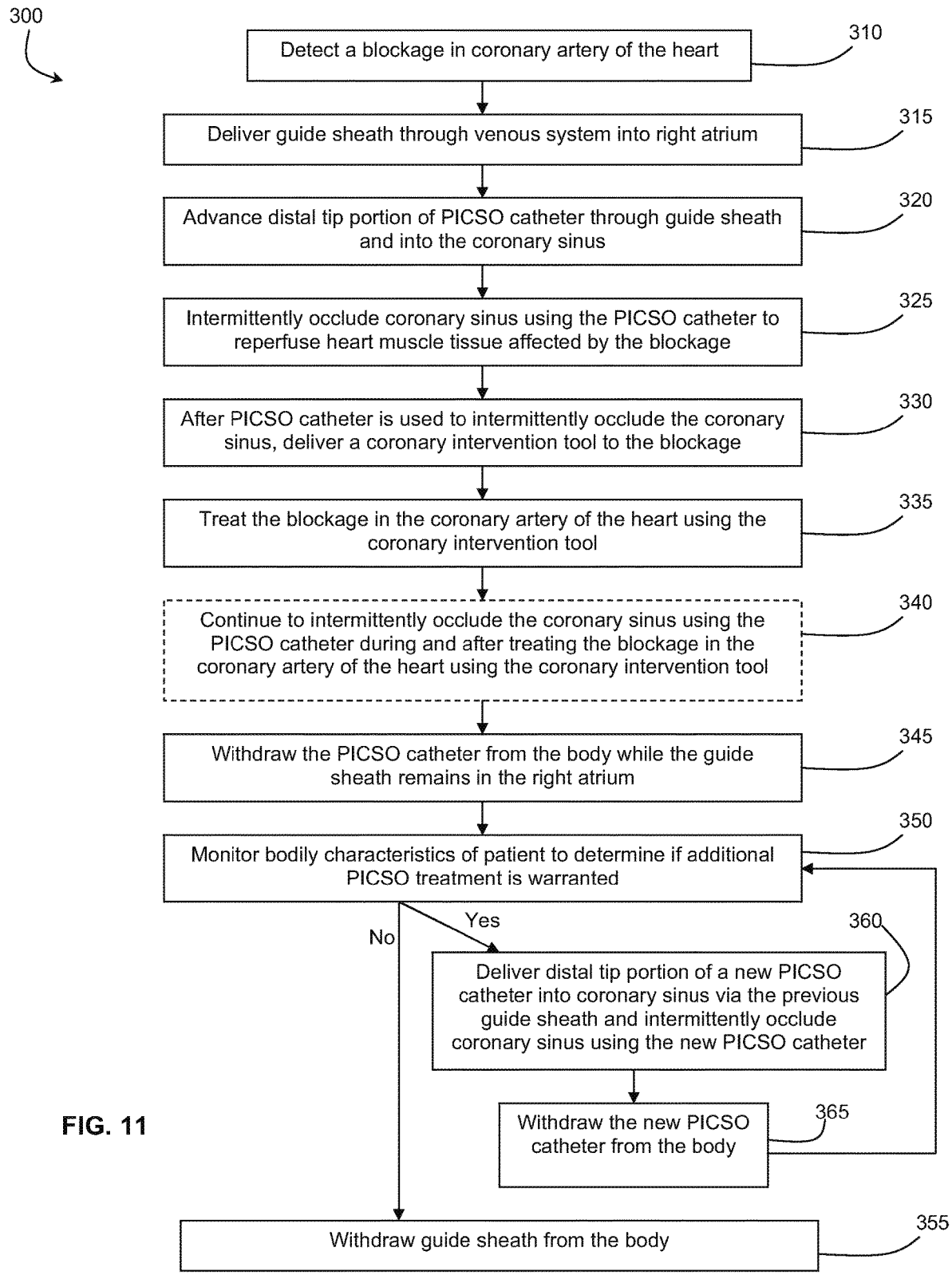
FIG. 11 is a flow chart of a process for of treating heart tissue, in accordance with some implementations.

Referring now to FIG. 11, a process 300 of using the previously described system 100 can be implemented in combination with a cardiac interventional procedure for treating a blockage in the heart. For example, in some implementations, the process 300 can include the step 310 of detecting a blockage in a heart, such as a blockage in a coronary arterial of the heart (refer, for example, to FIG. 1). In step 315, the process 300 may include delivering a guide sheath or other guide member through the venous system and into the right atrium (refer, for example, to the sheath 110 in FIG. 1). Also, in step 320, the process 300 may include advancing a distal tip portion of a coronary sinus occlusion catheter through the guide sheath and into the coronary sinus. For example, the catheter may be controlled by the control unit 140 so that it operates as a PICSO (pressure-controlled intermittent coronary sinus occlusion) catheter. In step 325, the process 300 may include the operation of intermittently occluding the coronary sinus using the PICSO catheter to reperfuse heart muscle tissue affected by the blockage (refer, for example, to FIG. 8). The timing of the intermittent occlusion and non-occlusion periods may be automatically controlled by the control unit 140.

The process 300 may include a step 330 of delivering a coronary intervention tool (e.g., a stent device, an angioplasty balloon, or the like) to the blockage in the coronary artery after the PICSO catheter is used to intermittently occlude the coronary sinus. In step 335, the coronary intervention tool can be used to treat the blockage in the coronary artery. Accordingly, the PICSO catheter described in step 325 can be employed to "pretreat" to the heart tissue affected by the blockage before the blockage is repaired using the coronary intervention tool.

Optionally, the process 300 may include the step 340 in which the PICSO catheter is employed to continue to intermittently occlude the coronary sinus during and after the procedure in step 335 where the blockage is treated with the coronary intervention tool. In such circumstances, the heart muscle tissue that was affected by the blockage may continue to be reperfused with venous blood both during and after the procedure to repair the blockage.

As shown in step 345 of FIG. 1, the PICSO catheter can be withdrawn from the body while the guide sheath remains in the right atrium (refer, for example, to FIG. 10). As previously described, the guide sheath 110 can remain in the right atrium during a post-operative monitoring period so as to provide simplified access to the heart in the event a subsequent PICSO treatment is warranted. For example, in step 350, the process 300 includes monitoring bodily characteristics of the patient to determine if additional PICSO treatment in warranted. In some cases, blood samples may be tested to monitor bio-markers present in the blood that indicate the extent of ischemia or damaged heart muscle tissue. The measurement of the bio-markers present in the patient's blood may include a measurement of lactate, potassium, and other indicators of ischemic tissue. Further, the patient's ECG data can be monitored during this post-operative monitoring period. If the patient's bodily characteristics indicate that no further PICSO treatment is warranted, the process 300 may proceed to the step 355 in which the guide sheath is withdrawn from the patient's body. If, however, the patient's bodily characteristics indicate that additional PICSO treatment is warranted, the process 300 may proceed to step 360 in which a new PICSO catheter is delivered through the previous guide sheath. In this step, a distal tip portion of the new PICSO catheter can be delivered into the right atrium, and the control unit can be employed to cause the new PICSO catheter to intermittently occlude the coronary sinus. In step 365, the new PICSO catheter can be withdrawn from the body after the additional PICSO treatment while the guide sheath remains in the right atrium (refer, for example, to FIG. 10). The process 300 may then return to step 350 in which the guide sheath 110 can remain in the right atrium during a post-operative monitoring period.

A number of embodiments of the invention have been described. Nevertheless, it will be understood that various modifications may be made without departing from the scope of the invention. Accordingly, other embodiments are within the scope of the following claims.

What is claimed is:

1. A system for treating heart muscle tissue, comprising:
   a coronary sinus occlusion catheter including a distal tip portion, a proximal hub portion, and a balloon fluid lumen, the distal tip portion of the coronary sinus occlusion catheter comprising an inflatable balloon device configured to occlude a coronary sinus when inflated with fluid via the balloon fluid lumen; and
   a control system to control inflation and deflation of the inflatable balloon device for intermittent coronary sinus occlusion, the control system comprising a display device, a pressure signal input that receives a pressure signal indicative of coronary sinus pressure, an electrocardiogram (ECG) signal input, and a control circuit that activates a pneumatic subsystem to inflate or deflate the inflatable balloon device of the coronary sinus occlusion catheter for intermittently occluding the coronary sinus,
   wherein the control system, during a first period of operation, is programmed to activate the inflatable balloon device of the coronary sinus occlusion catheter to intermittently occlude the coronary sinus according to an automated and predetermined first pattern of occlusion periods and release periods that is stored by the control system, the occlusion periods and the release periods of the first pattern having predetermined lengths of time that are independent of the pressure signal indicative of the coronary sinus pressure, and
   wherein the control system, during a second period of operation and after the first period of operation, is programmed to activate the inflatable balloon device of the coronary sinus occlusion catheter to intermittently occlude the coronary sinus in a second pattern of occlusion periods and release periods, the occlusion periods and the release periods of the second pattern being dependent at least in part on the pressure signal.

2. The system of claim 1, wherein the predetermined lengths of time of the occlusion periods of the first pattern are selected from a range of 6 seconds to 20 second, and the predetermined lengths of time of the release periods of the first pattern are selected from a range of 3 second to 7 seconds.

3. The system of claim 1, wherein the display device of the control system shows a graph of the pressure signal indicative of the coronary sinus pressure during intermittent occlusion of the coronary sinus.

4. The system of claim 3, wherein the display device of the control system shows a first time value indicative of a period of occlusion of the coronary sinus and a second time value indicative of a period of non-occlusion of the coronary sinus, the first and second time values being displayed contemporaneously with the graph of the pressure signal indicative of the coronary sinus pressure.

5. The system of claim 1, wherein the inflatable balloon device of the coronary sinus occlusion catheter has an outer diameter that is sized to occlude blood flow exiting from the coronary sinus and into a right atrium.

6. The system of claim 1, wherein the distal tip portion of the coronary sinus occlusion catheter includes a plurality of distal ports that are positioned distally forward of the inflatable balloon device.

7. The system of claim 6, wherein the distal ports face in a generally radially outward direction and are substantially uniformly spaced apart from one another along a circumference of the distal tip portion.

8. The system of claim 6, wherein the distal ports are all in fluid communication with a pressure sensor lumen of the coronary sinus occlusion catheter.

9. The system of claim 1, wherein the display device of the control system provides a graphical user interface that outputs time-sensitive data measurements indicative of a progress of a coronary sinus occlusion procedure.

10. The system of claim 9, wherein the graphical user interface of the display device outputs coronary sinus pressure data in a graph form for monitoring a trend of coronary sinus pressure measurements.

11. The system of claim 10, wherein the graphical user interface of the display device outputs numeric pressure measurements indicative of a maximum coronary sinus pressure and a minimum coronary sinus pressure.

12. The system of claim 11, wherein the graphical user interface of the display device outputs a numeric measurement of a non-occluded time in units of seconds.

13. The system of claim 9, further comprising one or more ECG sensors connectable to the control system, wherein the graphical user interface of the display device outputs ECG measurement data in a graph form.

14. The system of claim 9, wherein the graphical user interface of the display device outputs a numeric measurement of an occluded time in units of seconds.

15. The system of claim 1, wherein the control system is configured to compare the coronary sinus pressure at different times during the first period of operation to adjust the second pattern of occlusion periods and release periods of the second period of operation.

16. A system for treating heart muscle tissue, comprising:
a coronary sinus occlusion catheter including a distal tip portion, a proximal hub portion, and a balloon fluid lumen, the distal tip portion of the coronary sinus occlusion catheter comprising an inflatable balloon device configured to occlude a coronary sinus when inflated with fluid via the balloon fluid lumen; and
a control system to control inflation and deflation of the inflatable balloon device for intermittent coronary sinus occlusion, the control system comprising a display device, a pressure signal input that receives a pressure signal indicative of coronary sinus pressure, an electrocardiogram (ECG) signal input, and a control circuit that activates a pneumatic subsystem to inflate or deflate the inflatable balloon device of the coronary sinus occlusion catheter for intermittently occluding the coronary sinus,
wherein the control system, during a first period of operation, is programmed to activate the inflatable balloon device of the coronary sinus occlusion catheter to intermittently occlude the coronary sinus according to an automated and predetermined first pattern of occlusion periods and release periods that is stored by the control system and that is independent of the pressure signal indicative of the coronary sinus pressure, the occlusion periods and the release periods of the first pattern having predetermined lengths of time that are independent of the pressure signal, and
wherein the control system, during a second period of operation and after the first period of operation, is programmed to activate the inflatable balloon device of the coronary sinus occlusion catheter to intermittently occlude the coronary sinus in a second pattern of occlusion periods and release periods, the occlusion periods and the release periods of the second pattern being dependent at least in part on the pressure signal, and
wherein during a third period of operation after the second period of operation, the control system repeats the first pattern of occlusion periods and release periods that is previously stored by the control system and that is independent of the pressure signal indicative of the coronary sinus pressure.

17. The system of claim 16, wherein the control system is configured to compare coronary sinus pressure characteristics resulting from the first pattern of occlusion periods and release periods during the third period of operation relative to coronary sinus pressure characteristics resulting from the first pattern of occlusion periods and release periods during the first period of operation.

* * * * *

UNITED STATES PATENT AND TRADEMARK OFFICE
CERTIFICATE OF CORRECTION

PATENT NO.         : 11,241,238 B2
APPLICATION NO.    : 13/925107
DATED              : February 8, 2022
INVENTOR(S)        : Mohl It is certified that error appears in the above-identified patent and that said Letters Patent is hereby corrected as shown below:

On the Title Page

Item (72) Inventor, please replace "Altenmarkt-Thennenberg" with -- Altenmarkt-Thenneberg --.

Signed and Sealed this
Twentieth Day of September, 2022

Katherine Kelly Vidal
Director of the United States Patent and Trademark Office